US011377583B2

(12) United States Patent
Bartels et al.

(10) Patent No.: US 11,377,583 B2
(45) Date of Patent: Jul. 5, 2022

(54) ALKENYL SUCCINIMIDES AND USE AS NATURAL GAS HYDRATE INHIBITORS

(71) Applicant: ChampionX USA Inc., Sugarland, TX (US)

(72) Inventors: Jeremy Wayne Bartels, Sugar Land, TX (US); Jeffrey Michael Servesko, Sugar Land, TX (US); Kousik Kundu, Houston, TX (US); Boyd Anthony Laurent, Pearland, TX (US); David Field Tarverdi, Riverside, IL (US); Prakasa Rao Anantaneni, Richmond, TX (US); Jeremy Moloney, Katy, TX (US)

(73) Assignee: ChampionX USA Inc., Sugar Land, TX (US)

( * ) Notice: Subject to any disclaimer, the term of this patent is extended or adjusted under 35 U.S.C. 154(b) by 80 days.

(21) Appl. No.: 16/665,874

(22) Filed: Oct. 28, 2019

(65) Prior Publication Data

US 2020/0131429 A1 Apr. 30, 2020

Related U.S. Application Data

(60) Provisional application No. 62/751,938, filed on Oct. 29, 2018.

(51) Int. Cl.
*C09K 8/52* (2006.01)
*C07C 211/22* (2006.01)
*C07D 207/404* (2006.01)

(52) U.S. Cl.
CPC .............. *C09K 8/52* (2013.01); *C07C 211/22* (2013.01); *C07D 207/404* (2013.01); *C09K 2208/22* (2013.01)

(58) Field of Classification Search
CPC . C09K 8/528; C09K 8/08; C09K 8/86; C09K 8/506; C09K 8/68; C09K 2208/12; C09K 8/52; C09K 2208/22; C09K 8/524; C07C 211/22; C07D 207/404; C10L 1/224; C10L 3/107
See application file for complete search history.

(56) References Cited

U.S. PATENT DOCUMENTS

| | | | |
|---|---|---|---|
| 2,568,876 A | 9/1951 | White et al. | |
| 3,585,256 A | 6/1971 | Fuest et al. | |
| 4,398,921 A | 8/1983 | Rifkin et al. | |
| 4,761,473 A | 8/1988 | Treybig et al. | |
| 5,122,616 A * | 6/1992 | Malfer | C07D 207/412 44/347 |
| 5,221,491 A | 6/1993 | Roper et al. | |
| 5,304,315 A | 4/1994 | Stover | |
| 5,328,624 A | 7/1994 | Chung | |
| 5,334,321 A | 8/1994 | Harrison et al. | |
| 5,588,973 A | 12/1996 | Blackborow et al. | |
| 6,878,799 B2 | 4/2005 | He | |
| 7,253,231 B2 | 8/2007 | Devlin et al. | |
| 7,645,726 B2 | 1/2010 | Loper | |
| 8,153,567 B2 | 4/2012 | Krull et al. | |
| 8,628,591 B2 | 1/2014 | Krull et al. | |
| 8,734,542 B2 | 5/2014 | Krull et al. | |
| 9,296,971 B2 | 3/2016 | Loper | |
| 2004/0167040 A1 * | 8/2004 | Dahlmann | C09K 8/54 508/244 |
| 2006/0128571 A1 | 6/2006 | Loper | |
| 2010/0180492 A1 | 7/2010 | Krull et al. | |
| 2013/0085235 A1 | 4/2013 | Harrison et al. | |
| 2016/0122619 A1 | 5/2016 | Lucente-Schultz et al. | |
| 2017/0292083 A1 * | 10/2017 | Diegelmann | C10M 133/56 |
| 2019/0136146 A1 | 5/2019 | Chang et al. | |

FOREIGN PATENT DOCUMENTS

| | | | |
|---|---|---|---|
| EP | 0323774 | * | 7/1989 |
| EP | 0323774 A1 | | 7/1989 |
| EP | 2990469 A1 | | 3/2016 |
| WO | 9800493 | | 1/1998 |
| WO | 9800503 | | 1/1998 |
| WO | 2009135877 A1 | | 11/2009 |
| WO | 2016145018 A1 | | 9/2016 |
| WO | 2017223306 A1 | | 12/2017 |
| WO | WO2017/223306 | * | 12/2017 |

OTHER PUBLICATIONS

Silin et al. (2012) "Synthesis and testing of polyalkenyl succinimides as components of detergent additives for motor fuels", Petroleum Chemistry, 52(4):272-277.

Candy et al. (2005) "Synthesis and characterization of oleic succinic anhydrides: Structure-property relations", Journal of the American Oil Chemists' Society, 82(4):271-277.

Son et al. (2017) "Enhancement of the Dispersion of Asphaltenes in Heavy Crude Oil by the Addition of Poly(Butylene Succinic Anhydride)-based Dispersants", Bulletin of the Korean Checmical Society, 38(4):429-437.

* cited by examiner

*Primary Examiner* — Kumar R Bhushan
(74) *Attorney, Agent, or Firm* — Kagan Binder, PLLC

(57) ABSTRACT

Disclosed are succinimide-based compounds used in compositions and methods for inhibiting natural gas hydrate agglomerates. The succinimide-based compounds are reaction products of an alkenyl succinic anhydride and an amine or amine alcohol.

14 Claims, 2 Drawing Sheets

ALKENYL SUCCINIMIDES AND USE AS NATURAL GAS HYDRATE INHIBITORS

CROSS REFERENCE TO RELATED APPLICATIONS

This application claims the benefit of U.S. Provisional Patent Application Ser. No. 62/751,938, filed Oct. 29, 2018, the disclosure of which is herein incorporated by reference in its entirety.

FIELD OF THE INVENTION

The application is directed at inhibiting or preventing the formation of natural gas hydrate agglomerates.

BACKGROUND

"Natural gas hydrates" is a term referring to ice-like solids that are formed from gas molecules and water dissolved within liquid petroleum products (liquid hydrocarbons) when the temperature of the liquid is lowered and/or pressure upon the liquid is increased. Under these conditions, water molecules can form cage-like structures around gas molecules such as carbon dioxide, hydrogen sulfide, methane, ethane, propane, butane, and iso-butane, creating crystalline clathrate structures, also termed "clathrate gas hydrates." The specific architecture of a cage structure can be one of several types (called type 1, type 2, type H), depending on the identity of the guest molecule(s).

Once formed, these crystalline cage structures tend to precipitate and settle out from the liquid, accumulating into large solid masses. Such masses that form in petroleum liquids such as oil obtained from a subterranean reservoir can travel in transporting pipelines, and potentially block or damage the pipelines, related equipment, or both. The damage resulting from a blockage can be costly because equipment and pipelines need to be repaired, and oil production and the safety of field workers can be adversely affected.

Petroleum liquid recovery and production commonly operate under high pumping speed and high pressure within processing and transportation pipelines, conditions particularly favorable for natural gas hydrate formation. Additionally, weather conditions in some field locations can cause a substantial drop in temperature during one or more production, transportation, and storage operations carried out during and after recovery of liquids obtained from subterranean reservoirs.

The industry uses a number of methods to prevent or reduce natural gas hydrate formation and its accompanying adverse effects. For example, natural gas hydrate inhibitors include thermodynamic gas hydrate inhibitors (THI), anti-agglomerant gas hydrate inhibitors (AAs), and kinetic gas hydrate inhibitors (KHIs). The amount of chemical needed to prevent blockages varies widely depending upon the inhibitor type employed. THIs are substances that can reduce the temperature at which the gas hydrates form at a given pressure and water content, and are typically dosed at 50% based on water content and as high as 100% of the volume of water. Therefore, there is a substantial cost associated with the transportation and storage of large quantities of these inhibitors. A more cost-effective alternative is the use of low dosage gas hydrate inhibitors (LDHIs), as they generally require a dose of less than about 2 volume percent to inhibit the nucleation or growth of gas hydrates. The two general types of LDHIs, KHIs and anti-agglomerants, typically are used at much lower concentrations.

KHIs work by delaying the growth of gas hydrate crystals. They also function as anti-nucleators. In contrast, AAs allow natural gas hydrates to form but prevent them from agglomerating and subsequently accumulating into larger masses capable of causing plugs. AAs function to keep natural gas hydrate crystals and agglomerates dispersed as a slurry within the liquid hydrocarbon.

While many inhibitors and dispersants have been developed for ameliorating the effects of natural gas hydrates within liquid petroleum products, there continues to be a need for new and effective compositions and methods of preventing or reducing natural gas hydrate agglomerate formation.

SUMMARY

Described herein are compositions and methods for inhibiting the formation of natural gas hydrate agglomerates in a fluid comprising water, gaseous molecules, and a liquid hydrocarbon.

In one aspect of the invention is a composition comprising at least one succinimide-based compound to inhibit formation of natural gas hydrate agglomerates, the at least one succinimide-based compound formed by a reaction between an alkenyl succinic anhydride with an amine or amine alcohol.

In another aspect of the invention is a composition comprising:
 a fluid; and
 the at least one succinimide-based compound, the at least one succinimide-based compound formed by a reaction between an alkenyl succinic anhydride with an amine or amine alcohol.

In yet another aspect of the invention is a method of inhibiting formation of agglomerates of natural gas hydrates comprising:
 introducing into a fluid a composition comprising at least one succinimide-based compound to inhibit formation of agglomerates of natural gas hydrates, the at least one succinimide-based compound formed by a reaction between an alkenyl succinic anhydride with an amine or amine alcohol.

DETAILED DESCRIPTION

Figure 1:
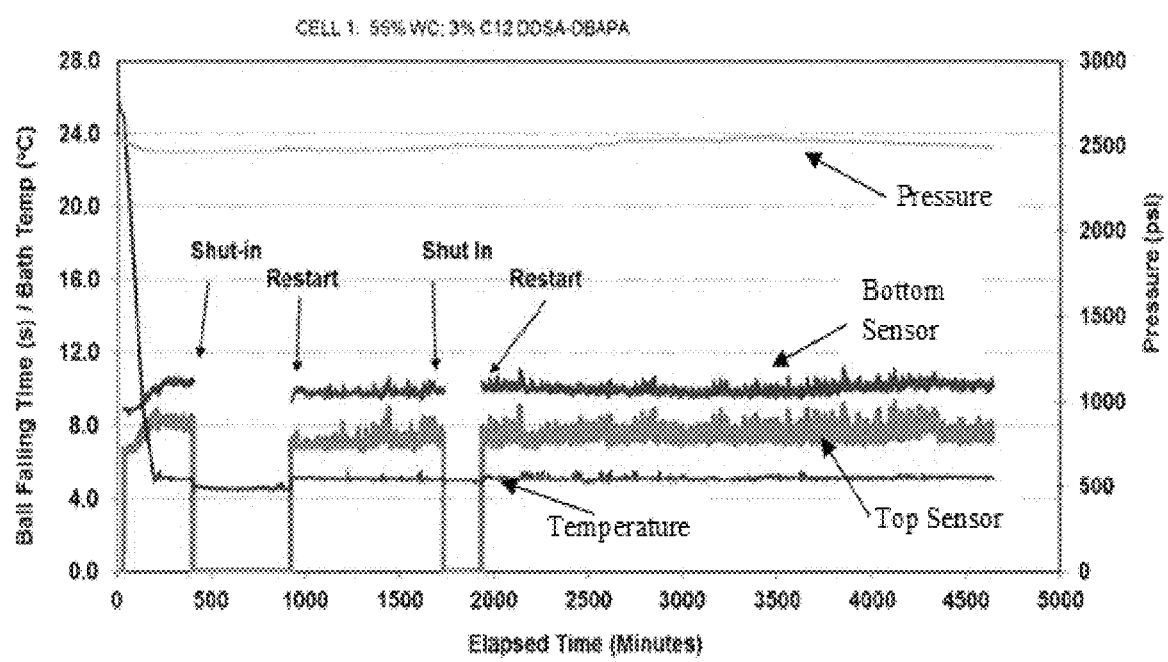
FIG. 1 is a graphical representation of cell pressure as a function of run time for a formulation of an embodiment of the invention.

Although the present disclosure provides references to various embodiments, persons skilled in the art will recognize that changes may be made in form and detail without departing from the spirit and scope of the invention. Various embodiments will be described in detail with reference to the figures. Reference to various embodiments does not limit the scope of the claims attached hereto. Additionally, any examples set forth in this specification are not intended to be limiting and merely set forth some of the many possible embodiments for the appended claims.

Unless otherwise defined, all technical and scientific terms used herein have the same meaning as commonly understood by one of ordinary skill in the art. In case of conflict, the present document, including definitions, will control. Methods and materials are described below, although methods and materials similar or equivalent to those described herein can be used in practice or testing of the present invention. All publications, patent applications, patents and other references mentioned herein are incorporated by reference in their entirety.

As used herein, the term "alkyl" refers to a monovalent group derived by the removal of a single hydrogen atom from a straight or branched chain or cyclic saturated or unsaturated hydrocarbon containing from one to sixty carbon atoms.

As used herein, the term "alkenyl" refers to an unsaturated hydrocarbon that contains at least one carbon-carbon double bound.

As used herein, the term "anti-agglomerant" or "AA" refers to a compound that inhibits formation of agglomerates of natural gas hydrates. The term will be understood to refer to the AA itself or in a composition which may include other AAs or compounds or solvents, as determined by context.

As used herein, the term "fluid" means liquid, gas molecules, or both in an oil or natural gas well production operation.

As used herein, the term "inhibits," "inhibiting," or grammatical equivalents thereof refers to preventing, retarding, mitigating, reducing, controlling and/or delaying formation of gas hydrates and/or agglomerates of gas hydrates, and/or equipment/pipeline plugs formed from gas hydrate agglomerates.

As used herein, the terms "natural gas hydrates" or "gas hydrates" refers to a gaseous mixture in a water clathrate.

As used herein, the terms "comprise(s)," "include(s)," "having," "has," "can," "contain(s)," and variants thereof are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "optional" or "optionally" means that the subsequently described event or circumstance may but need not occur, and that the description includes instances where the event or circumstance occurs and instances in which it does not.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe a range of values, for example "about 1 to 5" the recitation means "1 to 5" and "about 1 to about 5" and "1 to about 5" and "about 1 to 5" unless specifically limited by context.

As used herein, the term "substantially" means "consisting essentially of" and includes "consisting of" "Consisting essentially of" and "consisting of" are construed as in U.S. patent law. For example, a solution that is "substantially free" of a specified compound or material may be free of that compound or material, or may have a minor amount of that compound or material present, such as through unintended contamination, side reactions, or incomplete purification. A "minor amount" may be a trace, an unmeasurable amount, an amount that does not interfere with a value or property, or some other amount as provided in context. A composition that has "substantially only" a provided list of components may consist of only those components, or have a trace amount of some other component present, or have one or more additional components that do not materially affect the properties of the composition. Additionally, "substantially" modifying, for example, the type or quantity of an ingredient in a composition, a property, a measurable quantity, a method, a value, or a range, employed in describing the embodiments of the disclosure, refers to a variation that does not affect the overall recited composition, property, quantity, method, value, or range thereof in a manner that negates an intended composition, property, quantity, method, value, or range. Where modified by the term "substantially" the claims appended hereto include equivalents according to this definition.

As used herein, any recited ranges of values contemplate all values within the range and are to be construed as support for claims reciting any sub-ranges having endpoints which are real number values within the recited range. By way of example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

Described are compositions and methods to inhibit formation of agglomerates of natural gas hydrates, and/or plugs formed from natural gas hydrate agglomerates within liquid hydrocarbon recovery, processing, transportation, and storage operations. The compositions may be applied to one or more liquid hydrocarbon products to inhibit plugging of annular spaces, such as pipes, transfer lines, valves, and the like, including equipment downhole where the conditions are conducive for the formation of gas hydrates.

In embodiments, the compounds used in the compositions and methods for inhibiting gas hydrate agglomerates are alkenyl succinimide-based compounds. The compounds are formed by the reaction of an alkene and an unsaturated dicarboxylic acid anhydrides followed by a reaction with an amine or an alcohol. In embodiments, the alkenyl succinimide is formed by the reaction of an alkenyl-substituted succinic acid or succinic anhydride with an amine or amine alcohol. The resultant alkenyl succinimide-based compound has the general formula shown below as formula I,

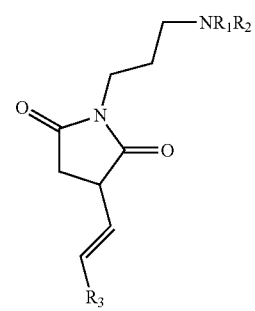

Formula I

Wherein, $R^1$=H or any 1-10 carbon saturated or unsaturated alkyl group, or a ring structure which would link to $R^2$, e.g., pyrrolidine or azepane;

Wherein, $R^2$=H or any 1-10 carbon saturated or unsaturated alkyl group or a ring structure which would link to $R^1$, e.g., pyrrolidine or azepane.

In embodiments, $R^1$ & $R^2$ are butyl, pentyl, isobutyl or isopentyl groups. In embodiments, $R^1$=$R^2$.

Wherein, $R^3$-alkyl or alkenyl chain or ring, saturated or unsaturated.

In embodiments, $R^3$ is an alkyl or alkenyl chain of 5-30 carbon atoms. In other embodiments, the $R^3$ is a 10 carbon atom, 18-22 carbon atoms, 20-24 carbon atoms, or mixtures thereof.

In embodiments, $R^1$ and $R^2$ each include one or more aminopropylamine chains such as dibutylaminopropylamine (DBAPA) or a DBAPA with additional aminopropylamine referred herein as dibutylaminopropylaminediamine or an extended DBAPA. In embodiments, $R^1$=$R^2$. In embodiments, $R^1$ and $R^2$ each are derived from the following amines:

Aminopropyl pyrrolidine

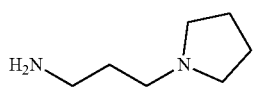

Aminopropyl azepane

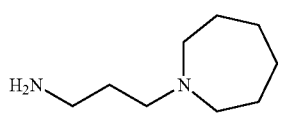

and

An extended dibutylaminopropylenediamine

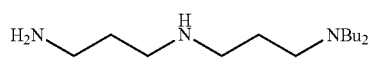

In embodiments, the succinimide-based compounds are shown below as formula II, with the various groups as previously described.

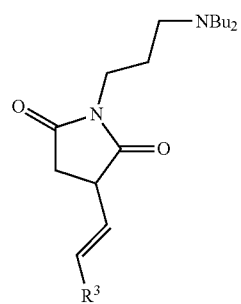

Formula II

The synthesis of the alkenyl succinimide-based compounds is not limited by the described processes. Any suitable method may be used to synthesize the alkenyl succinimide-based compounds.

In embodiments, the first stage is the generation of an alkenyl succinic anhydride moiety by the Alder-ene reaction. In embodiments, the Alder-ene reaction is a thermal reaction in which an unsaturated dicarboxylic acid is reacted with primary alkenes. In embodiments, the unsaturated dicarboxylic acid is a maleic acid. In embodiments, the reaction is as follows:

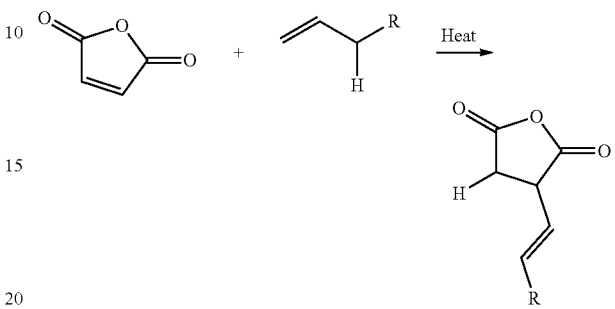

In embodiments, the Alder-ene reaction is carried at out at temperatures from 120° C. to about 250° C. for a period ranging from 1 to 48 hours. In embodiments the temperature is in the range from about 120° C. to about 160° C., from about 150° C. to about 250° C., from about 150° C. to about 225° C., or from about 180° C. to about 210° C. In embodiments the reaction is carried out from about 1-48 hours, 5-10 hours, 4-6 hours, 2-3 hours, 12-36 hours, 24-36 hours, or 24-48 hours. In embodiments, the reaction of the anhydride (e.g. maleic anhydride) and primary alkene are in a ratio of 1:1.

Various reaction modifiers, such as catalyst to promote the ene reaction or suppress tar formation and other materials and techniques to reduce by-product formation known in the art can be used in the present process. See for example U.S. Pat. Nos. 3,412,111; 3,819,660; 4,255,340 and 4,396,774, 8,242,287 the disclosures of which are incorporated herein by reference.

In embodiments, a second stage is the reaction between the alkyl or alkenyl succinic anhydride and an amine or alcohol. In embodiments, the resultant succinimide-based compounds may be formed by reaction with an alkenyl succinic anhydride and a dibutylaminopropylamine as shown below:

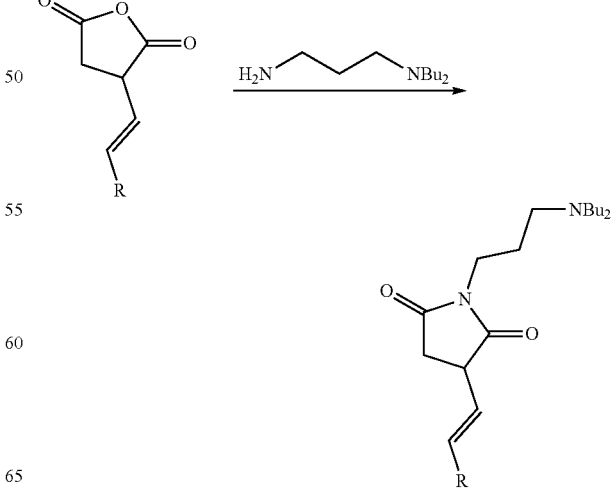

The second stage is carried out at ambient temperatures, followed by cooling, if desired. In embodiments, the ratio of the alkyl or alkenyl succinic anhydride to amine is 1:1 to about 3:1 or greater. In embodiments the ratio is from 10:1; 8:1; 6:1; or 3:1, with the most suitable ratios when the alkyl or alkenyl succinic anhydride is greater than the amine.

In embodiments, the alkene is a 2 to 30 carbon atom with at least one carbon-carbon double bound. In embodiments the alkene has one carbon-carbon double bound (mono-enes). The alkene can be linear or branched variants thereof and mixtures thereof. In embodiments the mono-enes are propylene, butene-1, pentene-1, hexene-1, heptene-1, octene-1, nonene-1, decene-1, undecene-1, dodecene-1, tridecene-1, tetradecene-1, pentadecene-1, hexadecene-1, heptadecene-1, octadcene-1, nonadecene-1, eicosene-1, heneicosene-1, docosene-1, tricosene-1, tetracosene-1, pentacosene-1, hexacosene-1, heptacosene and the like.

In embodiments, the alkene is 18-24 carbon atoms of a 1-alkene, 20-24 or mixtures thereof.

Any suitable amine may be used to react with the alkenyl succinic anhydride to result in the described succinimide-based compound. The amine may be characterized by the presence of at least one primary, secondary or tertiary amino group.

In embodiments, the amine is a monoamine, diamine, polyamine or combination thereof. Examples of monoamines include ethylamine, dimethylamine, diethylamine, n-butylamine, dibutylamine, allylamine, isobutylamine, cocoamine, stearylamine, laurylamine, methyllaurylamine, oleylamine, N-methyl-octylamine, dodecyl-amine, diethanolamine, morpholine, and octadecyl amine.

In embodiments, the amines are diamines, which can include aliphatic diamines, branched aliphatic diamines, cyclic diamines.

In embodiments, the polyamines have the formula [$R^5$—NH—$R^6$], wherein $R^5$ and $R^6$ are a H or an alkyl group.

In embodiments, the amine is a dibutylaminopropylenediamine:

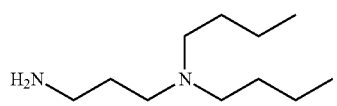

In embodiments, the amine is a dibutylaminopropylenediamine with an additional aminopropylamine:

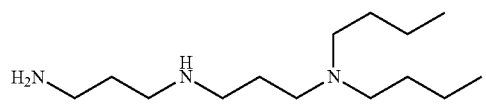 [SMILES: CCCCN(CCCC)CCCNCCCN]

In embodiments, the amine is an aminopropyl pyrrolidine:

In embodiments, the amine is an aminopropyl azepane:

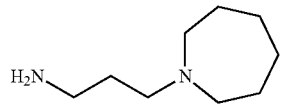 [SMILES: NCCCN1CCCCCC1]

In embodiments, polyalkylene polyamines of about 2 to 60, 2 to 40, 3 to 20 total carbon atoms and about 1 to 12, 3 to 12, 5 to 9 nitrogen atoms in the molecule.

In embodiments, amines are hydrocarbyl amines or hydrocarbyl amines including other groups, e.g., hydroxy groups, alkoxy groups, amide groups, nitriles, imidazoline groups, and the like. Hydroxy amines with 1 to 6 hydroxy groups or 1 to 3 hydroxy groups are useful.

In embodiments, amines are aliphatic saturated amines, including those of the general formulas:

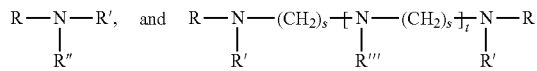

wherein R, R', R" and R'" are independently selected from a group of hydrogen; 1 to 25 carbon straight or branched chain alkyl radicals; 1 to 12 carbon alkoxy, 2 to 6 carbon alkylene radicals; 2 to 12 carbon hydroxy amino alkylene radicals; and 1 to 12 carbon alkylamino, 2 to 6 carbon alkylene radicals; and wherein R" can additionally comprise a moiety of the formula:

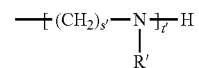

wherein R' is as defined above, and wherein s and s' can be the same or a different number of from 2 to 6, 2 to 4; and t and t' can be the same or different and are numbers of from 0 to 10, 2 to 7, or about 3 to 7, with the proviso that the sum of t and t' is not greater than 15.

In embodiments, exemplary amine compounds include: 1,2-diaminoethane; 1,3-diaminopropane; 1,4-diaminobutane; 1,6-diaminohexane: polyethylene amines such as diethylene triamine; triethylene tetramine; tetraethylene pentamine; polypropylene amines such as 1,2-propylene diamine; di-(1,2-propylene)triamine; di-(1,3-propylene) triamine; N,N-dimethyl-1,3-diaminopropane; N,N-di-(2-aminoethyl) ethylene diamine; N, N-di(2-hydroxyethyl)-1,3-propylene diamine; 3-dodecyloxypropylamine; N-dodecyl-1,3-propane diamine; tris hydroxymethylaminomethane (THAM); diisopropanol amine; diethanol amine; triethanol amine; mono-, di-, and tri-tallow amines; amino morpholines such as N-(3-aminopropyl)morpholine; and mixtures thereof.

Any suitable alcohol may be used to react with the alkenyl succinic anhydride to result in an a succinate ester compound.

In embodiments, the alkenyl succinic anhydride can react with a related amine alcohol to ring open the anhydride:

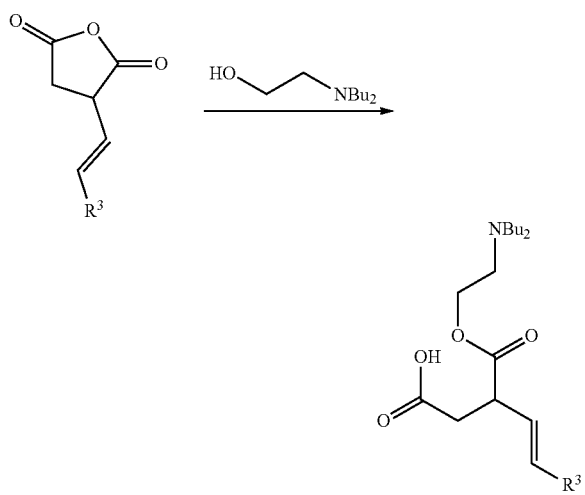

Wherein, $R^3$=alkyl or alkenyl chain or ring, saturated or unsaturated.

In embodiments, $R^3$ is an alkyl or alkenyl chain of 5-30 carbon atoms. In other embodiments, the $R^3$ is a 10 carbon atom, 18-22 carbon atoms, 20-24 carbon atoms, or mixtures thereof.

In embodiments, alcohols having the formula: OH—$R^4$ are used, wherein $R^4$ is an alkyl, aryl or alkaryl hydrocarbyl group having from one to twenty carbons, and wherein $R^4$ may be C1-C20 unsubstituted or substituted alkyl, C2-C20 unsubstituted or substituted alkenyl, C2-C20 unsubstituted or substituted alkynyl, C3-C20 unsubstituted or substituted cycloalkyl, C3-C20 unsubstituted or substituted cycloalkyl containing at least one heteroatom, C6-C20 unsubstituted or substituted aryl, C6-C20 unsubstituted or substituted aryl containing at least one heteroatom, C7-C20 unsubstituted or substituted alkaryl, or C7-C20 unsubstituted or substituted alkaryl containing at least one heteroatom.

In embodiments, the alcohols are methanol, ethanol, propanol, i-propanol, n-butanol, i-butanol, t-butanol, n-octanol, hexanol, cyclohexanol and benzyl alcohol or combinations thereof. In embodiments, the alcohol is an amino alcohol. Amino alcohols include the 2,2-disubstituted-2-amino-1-alkanols having from two to three hydroxy groups and containing a total of 4 to 8 carbon atoms. This amino alcohol can be represented by the formula:

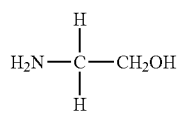

wherein X is an alkyl or hydroxyalkyl group with the alkyl groups having from 1 to 3 carbon atoms wherein at least one, and preferably both, of the X substituents is a hydroxyalkyl group of the structure —(CH$_2$)$_n$ OH, n being 1 to 3.

In embodiments, the alcohols are amino alcohols. Examples of amino alcohols include 2-amino-2-methyl-1,3 propanediol, 2-amino-2-ethyl-1,3-propanediol, and 2-amino-2-(hydroxymethyl)1,3-propanediol, (THAM or tris (hydroxymethyl) amino methane). In other embodiments, the alcohol is a dibutylaminoethanol, diethylaminoethanol, dipropylaminoethanol, diisopropyl, diisobutyl, diisopentyl, dipentyl and diisohexyl/dihexyl.

In embodiments, substituted succinic acid anhydrides with non-carbon containing chains that are terminated with an allyl or primary alkene are also used as anti-agglomerants:

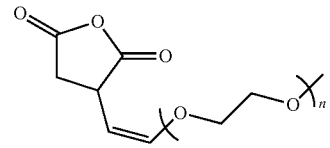

In embodiments, non-carbon containing chains are polyethylene glycol, polypropylene glycol, polyesters, polycarbonates, or polyamines.

In embodiments, an acidification step of a secondary or tertiary amines is generally achieved through the addition of an organic acid. Exemplary organic acids include acetic acid or acrylic acid. In other embodiments, the acrylic acid reactions with any residual primary or secondary amines (reversibly with tertiary amines) to yield a carboxybetaine structure. Other organic acids may be used for this acidification, including pivalic acid, malic acid, maleic acid, succinic acid, and any C1-C12+ carboxylic acids. Inorganic acids can also be used, such as common mineral acids (hydrochloric acid, phosphoric acid, nitric acid, carbonic acid) or related, as well as Lewis acids (tetrafluoroborate, aluminum trichloride, or the like).

The compositions and methods described herein are used to inhibit formation of agglomerates of gas hydrates, and plugging during liquid hydrocarbon production and transportation. In embodiments, compositions comprise, consist of, or consist essentially of at least one of the described succinimide-based compounds. In embodiments, the composition can further comprise one or more thermodynamic gas hydrate inhibitors, one or more kinetic gas hydrate inhibitors, one or more other AAs, or any combination thereof. In some embodiments, the composition can include other additives such as one or more asphaltene inhibitors, paraffin inhibitors, corrosion inhibitors, scale inhibitors, demulsifies, water clarifiers, dispersants, emulsion breakers, or any combination thereof.

The composition comprising the succinimide-based compounds is prepared or formulated in one or more solvents, depending upon the application and requirements. In embodiments, suitable solvents for formulation of compositions with the succinimide-based compounds include water, brine, seawater, alcohols such as methanol, ethanol, isopropanol, n-propanol, n-butanol, isobutanol, sec-butanol, t-butanol or higher alcohols such as benzyl alcohol); ketones such as acetone, or methyl ethyl ketone (2-butanone); acetonitrile; esters such as ethyl acetate, propyl acetate and butyl acetate; ethers such as diethyl ether or higher, e.g. methyl t-butyl ether, glyme, diglyme, ethylene glycol monobutyl ether, ethylene diglycol ethyl ether, 1,4 dioxane and related glycols; aromatics such as toluene, xylene(s), diethylbenzene, naphthalene and related aromatics or refinery cuts (heavy aromatic naptha, heavy aromatic distillates, and related); aliphatics such as pentane, hexane, heptane, octane, or refined gasoline; or several "green" solvents such as 2-methyltetrahydrofuran, furfural alcohol, and cyclopentylmethylether.

In embodiments, other solvents suitable for formulation with the succinimide-based compound include aliphatics, such as pentane, hexane, cyclohexane, methylcyclohexane, heptane, decane, dodecane, diesel, and the like, and aromatics, such as toluene, xylene, heavy aromatic naphtha, fatty acid derivatives (acids, esters, amides), and the like.

In embodiments, the succinimide-based compound is formulated in a composition with an amount from about 1-80 w/v %. In embodiments, the succinimide-based compound is added in an amount from about 1-10 w/v %, 10-20 w/v %, 20-60 w/v %, 45-60 w/v %, 60-80 w/v %, or 1-60 w/v %.

In embodiments, the composition comprising the succinimide-based compound is used in a method of inhibiting the formation of natural gas hydrate agglomerants. The method comprises adding to a fluid an amount of a composition comprising one or more succinimide-based compounds. In embodiments, the fluid comprises water, gas molecules, and liquid hydrocarbon.

An exemplary application point for the petroleum liquid production operations is near the surface controlled sub-sea safety valve. In embodiments, application or introduction of the succinimide-based compound is into a downhole. This ensures that during a shut-in, the composition is able to disperse throughout the area where natural gas hydrates will occur. Application of the succinimide-based compounds can also occur at other areas in the flowline, taking into account the density of the injected liquid. If the injection point is well above the gas hydrate formation depth, then the succinimide-based compound may be formulated with a solvent having a density high enough that the succinimide-based compound will sink in the flowline to collect at the water/oil interface. In embodiments, application is also used in pipelines or anywhere in the system where the potential for agglomerates of gas hydrate formation exists.

In embodiments, various dosage amounts of the succinimide-based compound or compositions containing them are introduced to the fluid to inhibit the formation of gas hydrate agglomerants. One of ordinary skill in the art is able to calculate the amount of a composition comprising the succinimide-based compound for a given situation without undue experimentation. Factors that would be considered important in such calculations include, for example, content of fluid, percentage water cut, API gravity of hydrocarbon. In embodiments, the succinimide-based compound alone or in a composition is introduced into a fluid to be treated from about 1000 ppm to about 50,000 ppm, from about 2000 ppm to about 15,000 ppm, or 3000 ppm to 20,000 ppm.

The composition and methods are useful for inhibiting gas hydrate agglomerate formation for many hydrocarbons and hydrocarbon mixtures. The compositions are particularly useful for lighter or low-boiling, 1-5 carbon containing hydrocarbon gases or gas mixtures at ambient conditions. In embodiments, the gases are methane, ethane, propane, n-butane, isobutane, isopentane, and mixtures thereof. In other embodiments, natural gas mixtures are present in many gas and/or oil formations and natural gas liquids. The hydrocarbons may also comprise other compounds including, but not limited to, carbon dioxide, hydrogen sulfide, and other compounds commonly found in gas/oil formations or processing plants, either naturally occurring and/or used in recovering/processing hydrocarbons from the formation, and mixtures thereof.

In embodiments, the compositions and methods are useful for inhibiting gas hydrate formation in a variety of black oils, heavy black oils to condensates, from API 20-50. In embodiments, the compositions and methods are useful for inhibiting gas hydrate formation in paraffinic or asphaltenic oils. In such embodiments, paraffin or asphaltene inhibitors are used in conjunction with the succinimide-based compounds.

In embodiments, the composition comprising the succinimide-based compound is applied to fluids that containing various levels of oil, brine or both having various levels of salinity. In one embodiment, the fluid has a salinity of about 0.1% to about 25% or about 10% to about 25% weight/weight (w/w).

In some embodiments, the composition comprising the succinimide-based compound is applied to a fluid that contains various levels of water cut. One of ordinary skill in the art understands that "water cut" refers to the percent of water in a composition containing an oil and water mixture. In one embodiment, the water cut is from about 1% to about 80% w/w with respect to the hydrocarbon phase. In other embodiments, the water cut is from about 1% to about 30% w/w, from about 5% to about 40% w/w, from about 10% to about 60% w/w, from about 15% to about 80% w/w with respect to the hydrocarbon phase.

The methods can be used at any pressure that results in hydrocarbon gas hydrates. When the hydrocarbons in the mixture are lower boiling hydrocarbons or hydrocarbon gases at ambient conditions, the pressure is usually at or greater than atmospheric pressure (e.g., about 101 kPa), greater than about 1 MPa, or greater than about 5 MPa. The pressure in certain formation or processing units or plants could be much higher, such as greater than about 20 MPa. There is no specific high-pressure limit.

The composition comprising the succinimide-based compound may be introduced by any method suitable for ensuring dispersal of the succinimide-based compound through the liquid being treated. In some embodiments, the succinimide-based compound may be injected prior to substantial formation of gas hydrates.

In some embodiments, the succinimide-based compound is introduced into fluid contained in an oil and gas pipeline. In other embodiments, the succinimide-based compound is added to fluid contained in refineries, such as separation vessels, dehydration units, gas lines, and pipelines. In embodiments, the succinimide-based compounds are introduced into a fluid using various well-known methods and they may be introduced at numerous, different locations throughout a given system. In other embodiments, the composition comprising the one or more succinimide-based compound is injected using mechanical equipment such as chemical injection pumps, piping tees, injection fittings, and the like.

The succinimide-based compounds are mixed or blended with mechanical mixing equipment or devices, stationary mixing setup or equipment, magnetic mixing or other suitable methods, to provide adequate contact and/or dispersion of the composition into the mixture. The introducing of the succinimide-based compound can be made in-line and/or offline. The various components of the composition may be mixed prior to and/or during introduction. One of skill will understand that the methods disclosed herein are not limited in any way by the timing or location of the introducing.

Below are described additional embodiments.

Embodiment 1

A composition comprising at least one succinimide-based compound to inhibit formation of natural gas hydrate agglomerates, the at least one succinimide-based compound formed by a reaction between an alkenyl succinic anhydride with an amine or amine alcohol.

Embodiment 2

The composition of embodiment 1, wherein the amine comprises primary, secondary or tertiary amine.

Embodiment 3

The composition as in one of embodiments 1-2, wherein the amine is a dibutylaminopropylenediamine, a dibutylaminopropylenediamine with an additional aminopropylamino moiety, or combination thereof.

Embodiment 4

The composition as in one of embodiments 1-3, wherein succinimide-based compounds is from about 1 wt/v % to about 80 wt/v % based on the composition.

Embodiment 5

The composition as in one of embodiments 1-4, wherein the composition further comprises one or more thermodynamic gas hydrate inhibitors, kinetic gas hydrate inhibitors, anti-agglomerants, asphaltene inhibitors, paraffin inhibitors, scale inhibitors, emulsifiers, water clarifiers, dispersants, emulsion breakers, or any combination thereof.

Embodiment 6

A composition comprising:
a fluid; and
the at least one succinimide-based compounds as in one of embodiments 1-5.

Embodiment 7

The composition as in one of embodiments 1-6, wherein the succinimide-based compounds are about is about 1000 ppm to 50,000 ppm.

Embodiment 8

The composition as in one of embodiments 6-7, wherein the fluid comprises water, natural gas, and liquid hydrocarbon.

Embodiment 9

A composition comprising succinimide-based compounds having the general formula:

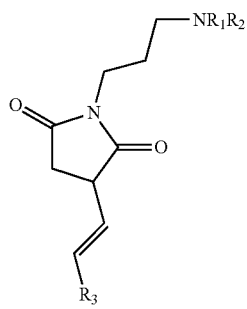

Wherein, $R_1$=H or any 1-10 carbon saturated or unsaturated alkyl group, or a ring structure which would link to $R_2$, e.g., pyrrolidine or azepane;
Wherein, $R_2$=H or any 1-10 carbon saturated or unsaturated alkyl group or a ring structure which would link to $R_1$, e.g., pyrrolidine or azepane;
Wherein, $R_3$=alkyl or alkenyl chain or ring, saturated or unsaturated.

Embodiment 10

A method of inhibiting formation of agglomerates of natural gas hydrates comprising:
introducing into a fluid a composition comprising at least one succinimide-based compound to inhibit formation of agglomerates of natural gas hydrates, the at least one succinimide-based compound formed by a reaction between an alkenyl succinic anhydride with an amine or amine alcohol.

Embodiment 11

The method of embodiment 10, wherein introducing is by injecting or pumping.

Embodiment 12

The method as in one of embodiments 10-11, wherein introducing is into a downhole.

Embodiment 13

The method as in one of embodiments 10-12, wherein the fluid is contained in an oil or natural gas production operation or pipeline.

Embodiment 14

The method as in one of embodiments 10-13, wherein the fluid comprises water, natural gas, and liquid hydrocarbon.

Embodiment 15

The method as in one of embodiments 10-14, wherein the fluid comprises water of about 1% to about 80% weight/weight with respect to a hydrocarbon phase.

Embodiment 16

The method as in one of embodiments 10-15, wherein the composition further comprises one or more thermodynamic gas hydrate inhibitors, kinetic gas hydrate inhibitors, anti-agglomerants, asphaltene inhibitors, paraffin inhibitors, scale inhibitors, emulsifiers, water clarifiers, dispersants, emulsion breakers, or any combination thereof.

Embodiment 17

The method as in one of embodiments 10-16, wherein the amine comprises primary, secondary or tertiary amine.

Embodiment 18

The method as in one of embodiments 10-17, wherein the amine comprises a dibutylaminopropylenediamine, a dibutylaminopropylenediamine with an additional aminopropylamino moiety, or combination thereof.

Embodiment 19

The method as in one of embodiments 10-18, wherein the succinimide-based compounds has the general formula:

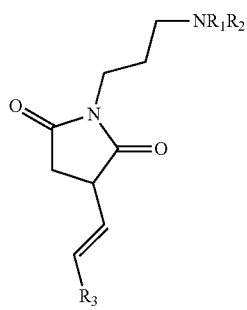

Wherein, R1=H or any 1-10 carbon saturated or unsaturated alkyl group, or a ring structure which would link to R2, e.g., pyrrolidine or azepane;

Wherein, R2=H or any 1-10 carbon saturated or unsaturated alkyl group or a ring structure which would link to R1, e.g., pyrrolidine or azepane;

Wherein, R3=alkyl or alkenyl chain or ring, saturated or unsaturated.

Embodiment 20

Use of the succinimide-based compound as in one of embodiments 1-19 to inhibit agglomerates of natural gas hydrates.

EXAMPLES

The following examples are intended to illustrate different aspects and embodiments of the invention and are not to be considered limiting the scope of the invention. It will be recognized that various modifications and changes may be made without following the experimental embodiments described herein, and without departing from the scope of the claims.

Example 1 Synthesis of C12 Alkenyl Succinic Anhydride and Dibutylaminopropylamine 50.0 g of dodecenyl succinimide (0.188 mol, 1.0 eq) was weighed into a 3 necked 250 mL round bottom flask. To this was added 34.98 g of dibutylaminopropylamine (0.188 mol, 1.0 eq) in a dropwise fashion. Once the addition was complete, the flask was equipped with a Dean-Stark trap and condenser. The contents were then heated to 120° C. (248° F.). Water was driven off over a period of 6 ours. Post reaction, the contents were cooled down to room temperature. The resultant product was acidified with acetic acid (11.27 g, 0.188 mol, 1.0 eq) and diluted to 50 wt % with 96.3 g methanol.

Example 2—Synthesis of C20-24 Alkenyl Succinic Anhydride and Dibutylaminopropylamine 50.0 g of C20/C24-alkenyl succinimide (0.188 mol, 1.0 eq) was weighed into a 3 necked 250 mL round bottom flask. To this was added 34.98 g of dibutylaminopropylamine (0.188 mol, 1.0 eq) in a dropwise fashion. Once the addition was complete, the flask was equipped with a Dean-Stark trap and condenser. The contents were then heated to 120° C. (248° F.). Water was driven off over a period of 6 hours. Post reaction, the contents were cooled down to room temperature. The resultant product was acidified with acetic acid (7.94 g, 0.188 mol, 1.0 eq) and diluted to 50 wt % with 82.5 g methanol.

Example 3

The rocking cell test was used to determine if the succinimide-based compounds are able to minimize gas hydrate agglomerate particles and disperse those particles into a hydrocarbon phase.

The rocking cell includes a rack on which individual cells are placed. Each individual cell includes a sapphire tubing containing a stainless steel ball inside the sapphire tubing. The stainless steel ball induces turbulence and mixes the liquids during the rocking process. The sapphire tubing can also withstand pressures up to about 5,000 psi. Once the cells are mounted onto the rack, the rack rocks up and down slowly, at a rate of about 1 complete cycle (up and down) per minute. The rack is further contained within a temperature controlled bath attached to a chiller.

The compositions include a hydrocarbon, an aqueous phase, a gas and the succinimide-based compound to be tested. The aqueous phase used was a brine of about 4% salinity and a water content of 55% of the composition. Various crude oils such as black oil, heavy black oil and condenstate were tested. A synthetic gas (~85% methane synthetic blend, which is a Type II gas hydrate forming gas blend) was used to pressurize the cells at the appropriate pressure. 2500 psi for the black oil and heavy black oil conditions, and 2000 psi for condensate.

Injected first into each cell was the brine and the gas. The succinimide-based compound was then dosed according to the amount of the brine in the test cell. The crude oil was heated to 60° C. for a minimum of 2 hours prior, then introduced into the cell containing the brine, gas, and the succinimide-based compound.

The cells with the test compositions were then equilibrated to a temperature of about 29° C., while rocking for 30 minutes.

The test is a constant pressure test where the cells are left open to a booster that boosts additional gas into the cells as gas was solubilized into the liquids and/or formed gas hydrates. The cells were rocked for about 30 minutes to equilibrate and mix prior to stopping at a horizontal position (shut-in). In the shut-in phase, the cells were cooled down to about 4.4° C. over approximately four hours and when the cells reached 4.4° C., they were rocked for an additional eight hours at 4.4° C. After a shut-in time of about 8 hours, the rocking of the cells was restarted for two hours. After two hours the cells were visually observed and ranked as pass/fail.

The pass/fail criteria were based on the ability of the ball in the rocking cell to move within the sapphire tube. For example, a succinimide-based compound tested was considered effective and passed the rocking cell test if at the time of the ranking, the ball moved freely when the cell was rocked indicating that few agglomerates were formed. In contrast, the succinimide-based compound failed if the ball's movement was obstructed or completely stopped by the formation of gas hydrate agglomerates. The anti-agglomerate's performance was considered borderline when there was observable gas hydrate agglomerates and at least some of the agglomerates stuck to the walls of the sapphire tube; when these agglomerates were present and the movement of the ball was not restricted, the succinimide-based compound ranking was considered borderline pass.

FIG. 1 shows the results for a succinimide-based compound (reaction between C12 alkyl succinic anhydride and dibutylaminopropylamine) as passing the rocking cell dosed at 3% with 55% water cut and 4% salinity in black oil.

Figure 2:
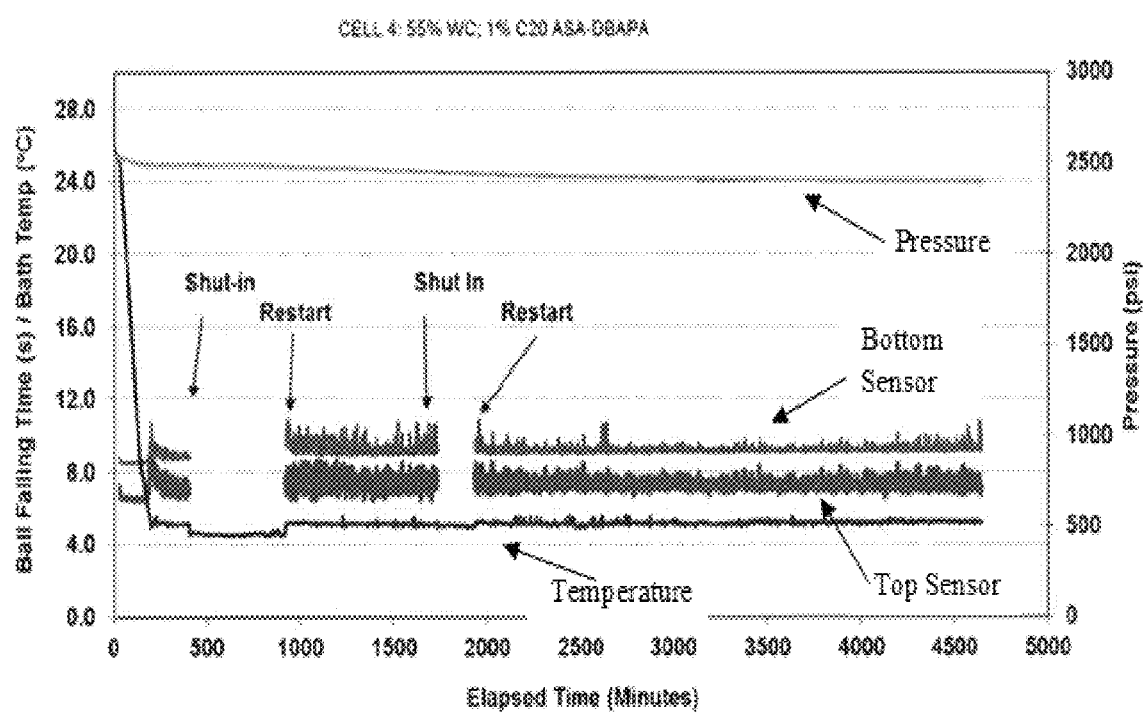
FIG. 2 is a graphical representation of cell pressure as a function of run time for a formulation of an embodiment of the invention.

FIG. 2 shows the results as passing the rocking cell test when the succinimide-based compound tested (reaction between C20-24 alkyl succinic anhydride and dibutylaminopropylamine) dosed at 1% with 55% water cut and 4% salinity in black oil.

What is claimed is:

1. A composition comprising succinimide-based compounds having the general formula:

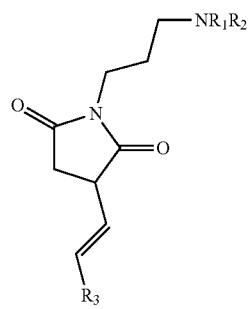

wherein $R^1$ is a ring structure linking to $R^2$,
wherein $R^2$ is a ring structure linking to $R^1$, and
wherein, $R^3$ is an alkyl or alkenyl chain or ring, saturated or unsaturated.

2. A method of inhibiting formation of agglomerates of natural gas hydrates comprising:
introducing into a fluid a composition comprising the succinimide-based compounds of claim 1 to inhibit formation of agglomerates of natural gas hydrates.

3. The method of claim 2, wherein introducing is by injecting or pumping.

4. The method of claim 2, wherein introducing is into a downhole.

5. The method of claim 2, wherein the fluid is contained in an oil or natural gas production operation or pipeline.

6. The method of claim 2, wherein the fluid comprises water, natural gas, and liquid hydrocarbon.

7. The method of claim 2, wherein the fluid comprises water of about 1% to about 80% weight/weight with respect to a hydrocarbon phase.

8. The method of claim 2, wherein the composition further comprises corrosion inhibitors, thermodynamic gas hydrate inhibitors, kinetic gas hydrate inhibitors, anti-agglomerants, asphaltene inhibitors, paraffin inhibitors, scale inhibitors, emulsifiers, water clarifiers, dispersants, emulsion breakers, or any combination thereof.

9. The composition of claim 1, wherein R1 and R2 are each selected from an aminopropyl pyrrolidine or aminopropyl azepine.

10. The composition of claim 1, wherein the succinimide-based compounds are from about 1 wt/v % to about 80 wt/v % based on the composition.

11. The composition of claim 1, wherein the composition further comprises corrosion inhibitors, thermodynamic gas hydrate inhibitors, kinetic gas hydrate inhibitors, anti-agglomerants, asphaltene inhibitors, paraffin inhibitors, scale inhibitors, emulsifiers, water clarifiers, dispersants, emulsion breakers, or any combination thereof.

12. A composition comprising:
a fluid; and
the succinimide-based compounds of claim 1.

13. The composition of claim 1, wherein the succinimide-based compounds are about 1000 ppm to 50,000 ppm.

14. The composition of claim 12, wherein the fluid comprises water, natural gas, and liquid hydrocarbon.

* * * * *